United States Patent
Kulkarni et al.

(10) Patent No.: US 9,814,516 B2
(45) Date of Patent: *Nov. 14, 2017

(54) DEPLOYMENT MECHANISMS FOR MULTI-FUNCTION SURGICAL INSTRUMENTS

(71) Applicant: COVIDIEN LP, Mansfield, MA (US)

(72) Inventors: Abhijit G. Kulkarni, Andhra Pradesh (IN); Amarsinh D. Jadhav, Islampur-Dist-Sangli (IN); Thiyagarajan Chelladurai, Tiruppur (IN)

(73) Assignee: COVIDIEN LP, Mansfield, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 14/543,200

(22) Filed: Nov. 17, 2014

(65) Prior Publication Data

US 2016/0135866 A1    May 19, 2016

(51) Int. Cl.
*A61B 18/12*   (2006.01)
*A61B 18/14*   (2006.01)
(Continued)

(52) U.S. Cl.
CPC ...... *A61B 18/1445* (2013.01); *A61B 2017/00367* (2013.01); *A61B 2017/2912* (2013.01);
(Continued)

(58) Field of Classification Search
CPC ............ A61B 18/1515; A61B 18/1442; A61B 18/1445; A61B 18/1447;
(Continued)

(56) References Cited

U.S. PATENT DOCUMENTS 5,312,391 A    5/1994   Wilk
5,318,589 A    6/1994   Lichtman
(Continued)

FOREIGN PATENT DOCUMENTS

EP    2679185 A1    1/2014

OTHER PUBLICATIONS

European Search Report issued in corresponding application No. EP 15191292.0 on Jan. 19, 2016.

*Primary Examiner* — Daniel Fowler (57) ABSTRACT

A surgical instrument includes a housing, a shaft, an end effector assembly disposed at the distal end of the shaft, a deployable assembly movable relative to the end effector assembly between a storage position and a deployed position, and a selector assembly. The selector assembly includes a selector member extending from the housing. The selector member is translatable relative to the housing between a first position and a second position. In the second position of the selector member, the selector member is rotatable relative to the housing for transitioning the selector assembly between a first state, wherein the selector member is decoupled relative to the deployable assembly, and a second state, wherein the selector member is coupled to the deployable assembly such that movement of the selector member from the second position to the first position effects movement of the deployable assembly from the storage position to the deployed position.

13 Claims, 7 Drawing Sheets (51) Int. Cl.
*A61B 17/00* (2006.01)
*A61B 17/29* (2006.01)
*A61B 18/00* (2006.01)

(52) U.S. Cl.
CPC .............. *A61B 2018/00607* (2013.01); *A61B 2018/126* (2013.01); *A61B 2018/1253* (2013.01); *A61B 2018/1422* (2013.01); *A61B 2018/1455* (2013.01); *A61B 2018/1467* (2013.01); *A61B 2018/1475* (2013.01)

(58) Field of Classification Search
CPC .... A61B 2018/0019; A61B 2018/0057; A61B 2018/1823; A61B 2018/1869; A61B 2018/1884; A61B 2018/145; A61B 2018/1452; A61B 2018/1455; A61B 2018/1457; A61N 5/02
See application file for complete search history.

(56) References Cited

U.S. PATENT DOCUMENTS

| | | | |
|---|---|---|---|
| 5,324,254 | A | 6/1994 | Phillips |
| 5,401,274 | A | 3/1995 | Kusunoki |
| 5,445,638 | A | 8/1995 | Rydell et al. |
| 5,458,598 | A | 10/1995 | Feinberg et al. |
| 5,556,397 | A | 9/1996 | Long et al. |
| 5,735,873 | A | 4/1998 | MacLean |
| 5,792,164 | A | 8/1998 | Lakatos et al. |
| 5,893,863 | A | 4/1999 | Yoon |
| 5,919,202 | A | 7/1999 | Yoon |
| 6,113,596 | A | 9/2000 | Hooven et al. |
| 6,156,009 | A | 12/2000 | Grabek |
| 6,190,386 | B1 | 2/2001 | Rydell |
| 6,270,497 | B1 | 8/2001 | Sekino et al. |
| 6,299,625 | B1 | 10/2001 | Bacher |
| 6,387,094 | B1 | 5/2002 | Eitenmuller |
| 6,551,313 | B1 | 4/2003 | Levin |
| 6,679,882 | B1 | 1/2004 | Kornerup |
| 6,699,206 | B2 | 3/2004 | Burbank et al. |
| 6,808,525 | B2 | 10/2004 | Latterell et al. |
| 6,942,662 | B2 | 9/2005 | Goble et al. |
| 7,033,356 | B2 | 4/2006 | Latterell et al. |
| 7,063,699 | B2 | 6/2006 | Hess et al. |
| 7,128,254 | B2 | 10/2006 | Shelton, IV et al. |
| 7,232,440 | B2 | 6/2007 | Dumbauld et al. |
| 7,367,976 | B2 | 5/2008 | Lawes et al. |
| 7,402,162 | B2 | 7/2008 | Ouchi |
| 7,445,621 | B2 | 11/2008 | Dumbauld et al. |
| 7,510,562 | B2 | 3/2009 | Lindsay |
| 7,588,570 | B2 | 9/2009 | Wakikaido et al. |
| 7,658,311 | B2 | 2/2010 | Boudreaux |
| 7,758,577 | B2 | 7/2010 | Nobis et al. |
| 7,815,636 | B2 | 10/2010 | Ortiz |
| 7,819,872 | B2 | 10/2010 | Johnson et al. |
| 8,257,352 | B2 | 9/2012 | Lawes et al. |
| 8,353,437 | B2 | 1/2013 | Boudreaux |
| 2002/0049442 | A1 | 4/2002 | Roberts et al. |
| 2004/0116920 | A1 | 6/2004 | Rioux et al. |
| 2004/0236326 | A1 | 11/2004 | Schulze et al. |
| 2005/0187547 | A1 | 8/2005 | Sugi |
| 2008/0215050 | A1 | 9/2008 | Bakos |
| 2009/0125026 | A1 | 5/2009 | Rioux et al. |
| 2009/0125027 | A1 | 5/2009 | Fischer |
| 2009/0131974 | A1 | 5/2009 | Pedersen et al. |
| 2009/0254084 | A1 | 10/2009 | Naito |
| 2010/0185196 | A1 | 7/2010 | Sakao et al. |
| 2010/0185197 | A1 | 7/2010 | Sakao et al. |
| 2010/0292690 | A1 | 11/2010 | Livneh |
| 2011/0087173 | A1 | 4/2011 | Sibbitt, Jr. et al. |
| 2011/0087218 | A1 | 4/2011 | Boudreaux et al. |
| 2011/0130757 | A1 | 6/2011 | Horlle et al. |
| 2011/0264093 | A1 | 10/2011 | Schall |
| 2012/0116396 | A1* | 5/2012 | Price ................ A61B 17/00234 606/45 |
| 2012/0330351 | A1 | 12/2012 | Friedman et al. |
| 2014/0046327 | A1 | 2/2014 | Tzachar et al. |
| 2014/0276797 | A1 | 9/2014 | Batchelor et al. |

\* cited by examiner

DEPLOYMENT MECHANISMS FOR MULTI-FUNCTION SURGICAL INSTRUMENTS

BACKGROUND

Technical Field

The present disclosure relates to surgical instruments and, more particularly, to deployment mechanisms for deploying, e.g., actuating, one or more components of a surgical instrument.

Background of Related Art

Many surgical instruments include one or more movable handles, levers, actuators, triggers, etc. for actuating and/or manipulating one or more functional components of the surgical instrument. For example, a surgical forceps may include a movable handle that is selectively compressible relative to a stationary handle for moving first and second jaw members of the forceps between spaced-apart and approximated positions for grasping tissue therebetween. Such a forceps may further include a trigger for selectively deploying a knife between the jaw members to cut tissue grasped therebetween.

As can be appreciated, as additional functional components are added to the surgical instrument, additional deployment structures or deployment structures capable of actuating more than one component are required. However, multiple deployment structures and/or combined deployment structures may be limited by spatial constraints within the housing of the surgical instrument, functional constraints of the components, e.g., where a combined deployment structure imparts additional force requirements for deploying one or more of the components coupled thereto, and/or may overly complicate the operable components of the surgical instrument.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

In accordance with aspects of the present disclosure, a surgical instrument is provided including a housing, a shaft extending distally from the housing, an end effector assembly disposed at a distal end of the shaft, a deployable assembly selectively movable relative to the end effector assembly between a storage position and a deployed position, and a selector assembly operably associated with the deployable assembly. The selector assembly includes a selector member extending from the housing for manual manipulation thereof. The selector member is manually translatable relative to the housing between a first position and a second position. In the second position of the selector member, the selector member is manually rotatable relative to the housing for transitioning the selector assembly between a first state, wherein the selector member is decoupled relative to the deployable assembly, and a second state, wherein the selector member is coupled to the deployable assembly such that movement of the selector member from the second position to the first position effects movement of the deployable assembly from the storage position to the deployed position.

In an aspect of the present disclosure, the end effector assembly includes first and second jaw members. One or both of the jaw members is movable relative to the other between a spaced-apart position and an approximated position for grasping tissue therebetween.

In another aspect of the present disclosure, each of the first and second jaw members includes an electrically-conductive tissue-contacting surface. The electrically-conductive tissue-contacting surfaces are configured to conduct energy therebetween and through tissue grasped between the first and second jaw members to treat tissue in a bipolar mode.

In another aspect of the present disclosure, the deployable assembly includes an energizable member and an insulative sleeve. The energizable member and insulative sleeve are configured to move together between the storage position and the deployed position. Further, the energizable member may be configured to conduct energy to tissue to treat tissue in a monopolar mode.

In still another aspect of the present disclosure, in the deployed position, the insulative sleeve is disposed about the end effector assembly and the energizable member extends distally from the end effector assembly.

In yet another aspect of the present disclosure, the first position of the selector member corresponds to a more-distal position of the selector member relative to the housing. In such aspects, the second position of the selector member corresponds to a more-proximal position of the selector member relative to the housing.

In still yet another aspect of the present disclosure, the deployable assembly includes an elongate member defining at least one cut-out and the selector assembly includes at least one arm defining at least one tab. Each tab is configured for receipt within one of the cut-outs when the selector member is disposed in the second position and the second state to engage the selector assembly with the deployable assembly.

In another aspect of the present disclosure, in the first state of the selector member, the deployable assembly is maintained in position during movement of the selector member between the first and second positions.

Another surgical instrument provided in accordance with aspects of the present disclosure includes a housing, a shaft extending distally from the housing, an end effector assembly disposed at a distal end of the shaft, a deployable assembly, and a selector assembly. The end effector assembly includes first and second jaw members. At least one of the first and second jaw members is movable relative to the other between a spaced-apart position and an approximated position for grasping tissue therebetween. The first and second jaw members are configured to conduct energy therebetween and through tissue grasped therebetween to treat tissue in a bipolar mode. The deployable assembly includes an insulative sleeve and an energizable member. The deployable assembly is selectively movable relative to the end effector assembly between a storage position, wherein the insulative sleeve and the energizable member are positioned proximally of the end effector assembly, and a deployed position, wherein the insulative sleeve is disposed about the end effector assembly and the energizable member extends distally from the end effector assembly. The selector assembly is operably associated with the deployable assembly and is transitionable between a disengaged condition, wherein the selector assembly is disengaged from the deployable assembly such that the deployable assembly is unaffected by movement of the selector assembly, and an engaged condition, wherein the selector assembly is engaged with the deployable assembly such that movement of the selector assembly moves the deployable assembly between the storage position and the deployed position.

In an aspect of the present disclosure, the selector assembly includes a selector member translatable relative to the housing between an inserted position, wherein the selector member extends into the housing, and a withdrawn position, wherein the selector member extends proximally from the housing, for moving the deployable assembly between the storage position and the deployed position when the selector assembly is disposed in the engaged condition.

In another aspect of the present disclosure, the deployable assembly is maintained in its position upon translation of the selector member between the inserted and withdrawn positions with the selector assembly disposed in the disengaged condition.

In yet another aspect of the present disclosure, rotation of the selector member from a first orientation to a second orientation with the selector member disposed in the withdrawn position transitions the selector assembly from the disengaged condition to the engaged condition.

In still another aspect of the present disclosure, the deployable assembly includes an elongate member defining at least one cut-out and the selector assembly includes at least one arm defining at least one tab. Each tab is received within one of the cut-outs when the selector assembly is disposed in the engaged condition to engage the selector assembly with the deployable assembly.

In still yet another aspect of the present disclosure, the at least one tab is offset from the respective cut-out in the disengaged condition of the selector assembly.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
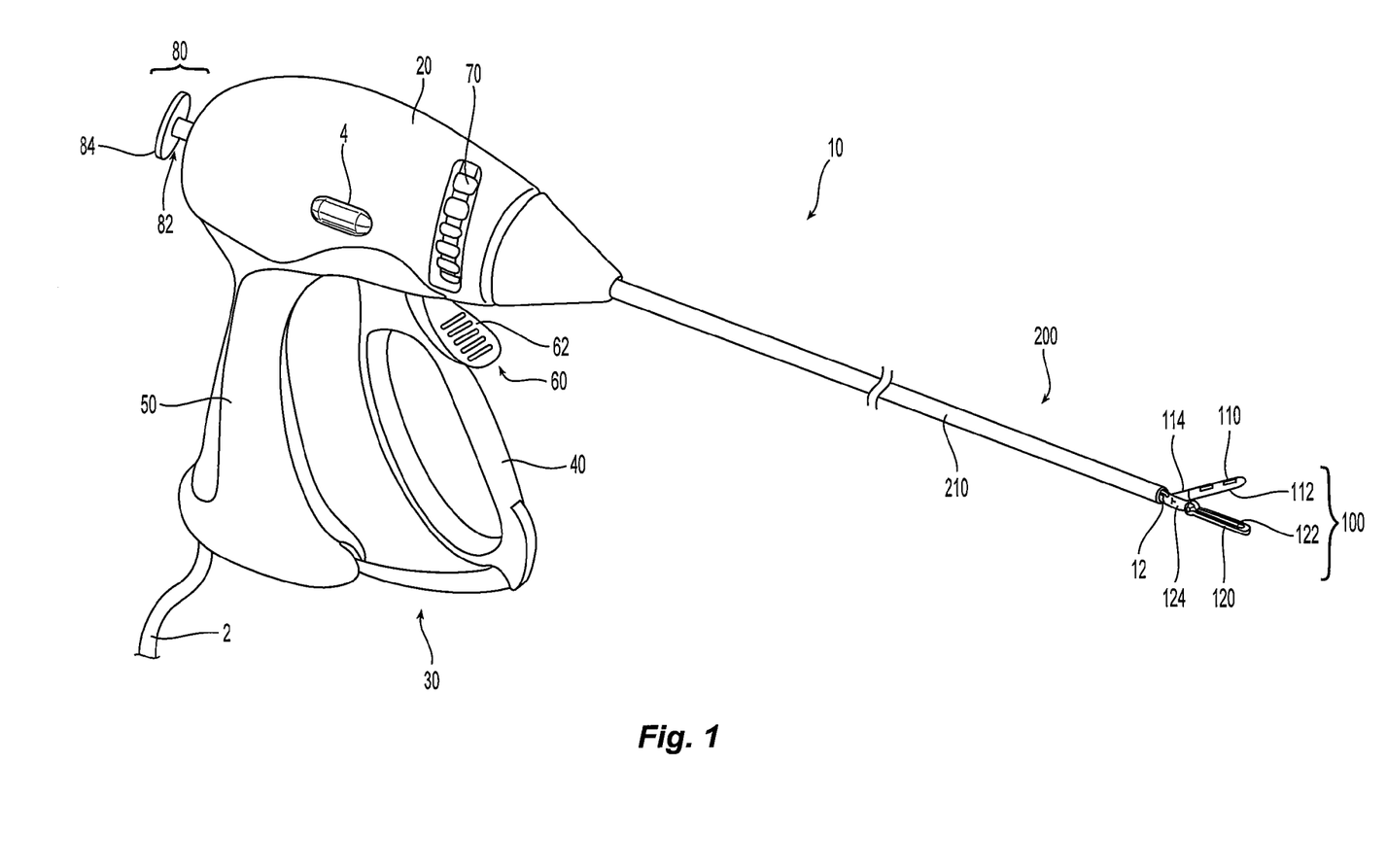
FIG. 1 is a front, perspective view of an endoscopic surgical forceps configured for use in accordance with the present disclosure.

Referring generally to FIG. 1, a forceps provided in accordance with the present disclosure is shown generally identified by reference numeral 10. Forceps 10, as will be described below, is configured to operate in both a bipolar mode, e.g., for grasping, treating, and/or dissecting tissue, and a monopolar mode, e.g., for treating and/or dissecting tissue. Although the present disclosure is shown and described with respect to forceps 10, the aspects and features of the present disclosure are equally applicable for use with any suitable surgical instrument or portion(s) thereof for selectively actuating, moving, and/or deploying the assemblies and/or components of the surgical instrument. Obviously, different connections and considerations apply to each particular instrument and the assemblies and/or components thereof; however, the aspects and features of the present disclosure remain generally consistent regardless of the particular instrument, assemblies, and/or components provided.

Continuing with reference to FIG. 1, forceps 10 includes a housing 20, a handle assembly 30, a trigger assembly 60, a rotating assembly 70, a selector assembly 80, an end effector assembly 100, and a deployable monopolar assembly 200. Forceps 10 further includes a shaft 12 having a distal end configured to mechanically engage end effector assembly 100 and a proximal end that mechanically engages housing 20. Forceps 10 also includes an electrosurgical cable 2 that connects forceps 10 to a generator (not shown) or other suitable power source, although forceps 10 may alternatively be configured as a battery powered instrument. Cable 2 includes wires (not shown) extending therethrough that have sufficient length to extend through shaft 12 in order to provide electrical energy to at least one electrically-conductive surface 112, 122 (FIG. 2A) of jaw members 110, 120, respectively, of end effector assembly 100, e.g., upon activation of activation switch 4 in a bipolar mode. One or more of the wires (not shown) of cable 2 extends through housing 20 in order to provide electrical energy to deployable monopolar assembly 200, e.g., upon activation of activation switch 4 in a monopolar mode. Rotating assembly 70 is rotatable in either direction to rotate end effector assembly 100 and deployable monopolar assembly 200 relative to housing 20. Housing 20 houses the internal working components of forceps 10, which are described in detail below.

Figure 2A:
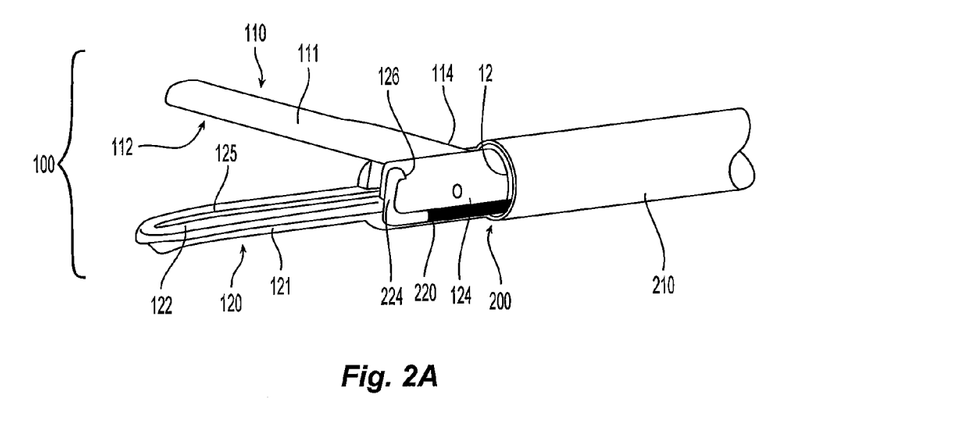
FIG. 2A is an enlarged, front, perspective view of an end effector assembly of the forceps of FIG. 1, wherein the jaw members of the end effector assembly are disposed in a spaced-apart position and wherein the monopolar assembly is disposed in a storage position.
Figure 2B:
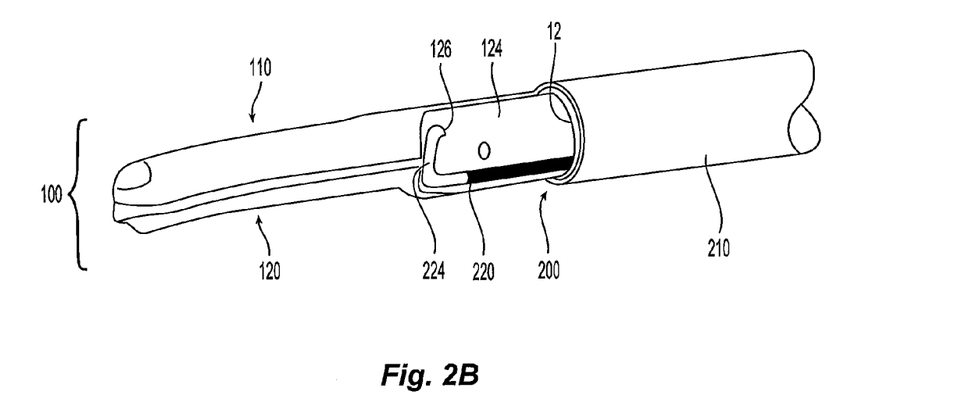
FIG. 2B is an enlarged, front, perspective view of the end effector assembly of FIG. 2A, wherein the jaw members are disposed in an approximated position and wherein the monopolar assembly is disposed in the storage position.
Figure 2C:
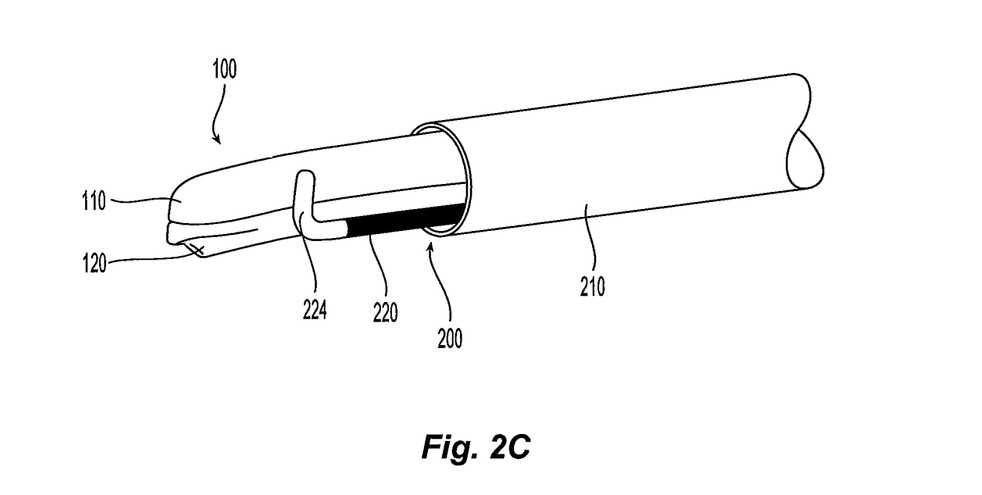
FIG. 2C is an enlarged, front, perspective view of the end effector assembly of FIG. 2A, wherein the jaw members are disposed in the approximated position and wherein the monopolar assembly is transitioning from the storage position to a deployed position.

Referring to FIGS. 2A and 2B, end effector assembly 100 is attached at a distal end of shaft 12 and includes opposing jaw members 110, 120 pivotably coupled to one another. Each of the jaw members 110 and 120 includes a jaw body 111, 121 supporting the respective electrically-conductive surface 112, 122, and a respective proximally-extending jaw flange 114, 124. Flanges 114, 124 are pivotably coupled to one another to permit movement of jaw members 110, 120 relative to one another between a spaced-apart position (FIG. 2A) and an approximated position (FIG. 2B) for grasping tissue between surfaces 112, 122. One or both of surfaces 112, 122 are adapted to connect to a source of energy (not explicitly shown), e.g., via the wires (not shown) of cable 2 (FIG. 1) and are configured to conduct energy through tissue grasped therebetween to treat, e.g., seal, tissue. More specifically, in some embodiments, end effector assembly 100 defines a bipolar configuration wherein surface 112 is charged to a first electrical potential and surface 122 is charged to a second, different electrical potential such that an electrical potential gradient is created for conducting energy between surfaces 112, 122 and through tissue grasped therebetween for treating e.g., sealing, tissue. Activation switch 4 (FIG. 1) is operably coupled between the source of energy (not shown) and surfaces 112, 122, thus allowing the user to selectively apply energy to surfaces 112, 122 of jaw members 110, 120, respectively, of end effector assembly 100 during a bipolar mode of operation.

End effector assembly 100 is designed as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments, a knife channel 115, 125 (FIGS. 3A and 3B) may be defined within one or both of jaw members 110, 120 to permit reciprocation of a knife 184 (FIGS. 3A and 3B) therethrough, e.g., upon actuation of a trigger 62 of trigger assembly 60, to cut tissue grasped between jaw members 110, 120.

Referring to FIGS. 2A-2D, 4, and 5, deployable monopolar assembly 200 includes an insulative sleeve 210, an energizable rod member 220, a proximal hub assembly 230 (FIGS. 4 and 5), and a biasing member (not shown). Insulative sleeve 210 is slidably disposed about shaft 12 and is selectively movable about and relative to shaft 12 and end effector assembly 100 between a storage position (FIG. 2B), wherein insulative sleeve 210 is disposed proximally of end effector assembly 100, and a deployed position (FIG. 2D), wherein insulative sleeve 210 is substantially disposed about end effector assembly 100 so as to electrically insulate surfaces 112, 122 of jaw members 110, 120, respectively, from the surroundings of insulative sleeve 210.

Figure 2D:
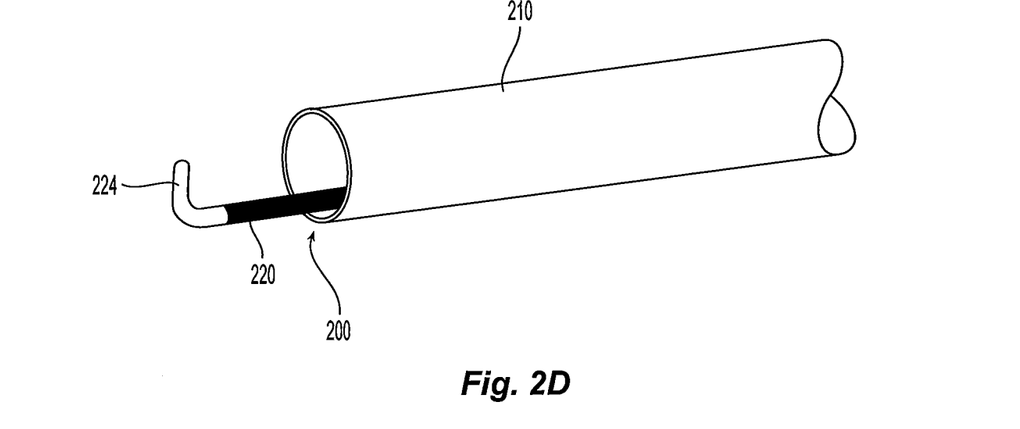
FIG. 2D is an enlarged, front, perspective view of the end effector assembly of FIG. 2A, wherein the monopolar assembly is disposed in the deployed position.

Energizable rod member 220 extends through sleeve 210 and distally therefrom, ultimately defining an electrically-conductive distal tip 224. Energizable rod member 220 and, more specifically, distal tip 224 thereof, functions as the active electrode of deployable monopolar assembly 200. The one or more wires (not shown) extending from cable 2 through housing 20 (see FIG. 1), are coupled to energizable rod member 220 to provide energy to energizable rod member 220, e.g., upon actuation of activation switch 4 (FIG. 1) in a monopolar mode, for treating tissue in a monopolar mode of operation. Energizable rod member 220 is movable between a storage position (FIG. 2B), wherein distal tip 224 of energizable rod member 220 is positioned adjacent proximal flange 124 of jaw member 120, and a deployed position (FIG. 2D), wherein distal tip 224 of rod member 220 extends distally from the distal ends of jaw members 110, 120. More specifically, in the storage position of energizable rod member 220, as shown in FIGS. 2A and 2B, distal tip 224 of energizable rod member 220 of deployable monopolar assembly 200 is disposed within insulated groove 126 defined within proximal flange 124 of jaw member 120, although other configurations are also contemplated. Insulated groove 126 electrically-insulates distal tip 224 of energizable rod member 220 from electrically-conductive surfaces 112, 122 of jaw members 110, 120, respectively, and from surrounding tissue when disposed in the storage position. Alternatively, distal tip 224 of energizable rod member 220 may only be insulated from surface 112 (or surface 122). In such configurations, distal tip 224 of energizable rod member 220 is capable of being energized to the same polarity as surface 122 (or surface 112). In the deployed position of energizable rod member 220, as shown in FIG. 2D, distal tip 224 of energizable rod member 220 extends distally from end effector assembly 100 and insulative sleeve 210, which substantially surrounds end effector assembly 100 in the deployed position. In this position, energy may be applied to distal tip 224 of energizable rod member 220 to treat tissue, e.g., via activation of activation switch 4 (FIG. 1) in the monopolar mode. Distal tip 224 may be hook-shaped (as shown), or may define any other suitable configuration, e.g., linear, circular, angled, etc.

Figure 4:
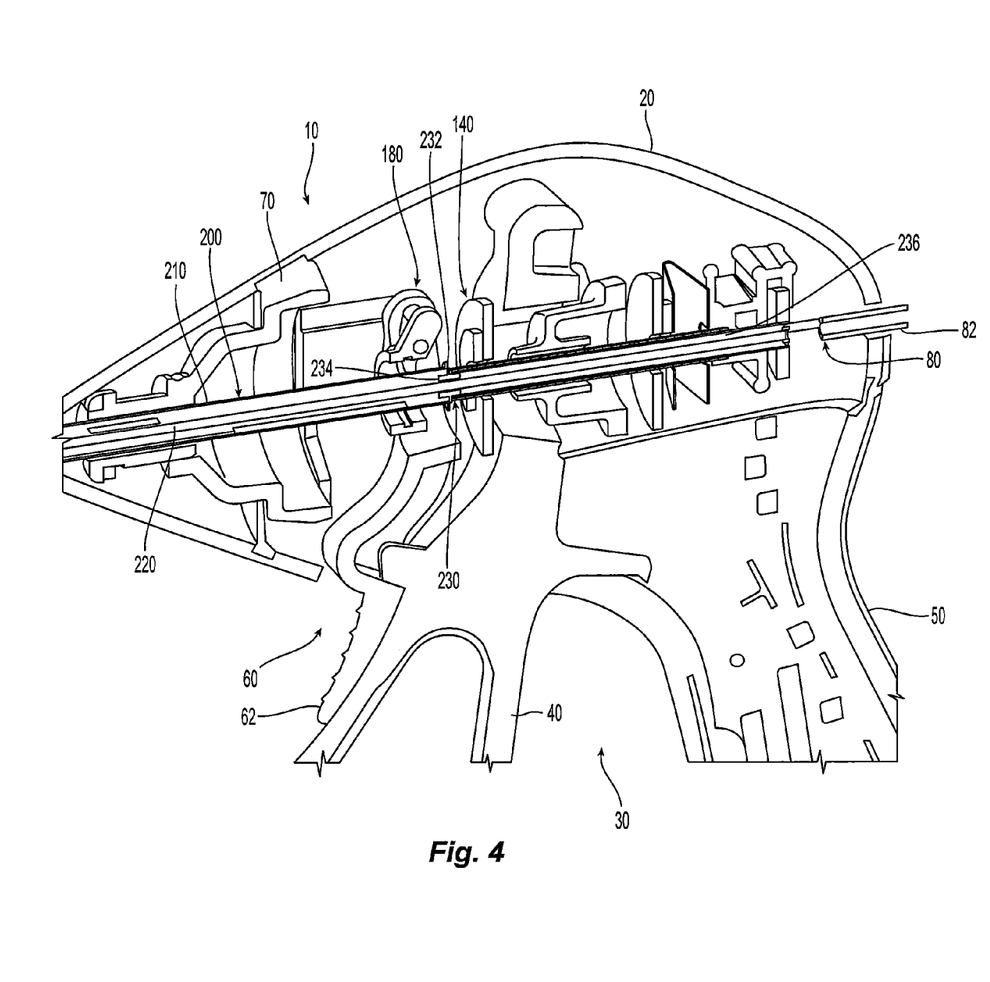
FIG. 4 is an enlarged, longitudinal, cross-sectional view of the proximal end of the forceps of FIG. 1 with portions removed to illustrate the internal components of the selector assembly and the monopolar assembly of the forceps of FIG. 1.
Figure 5:
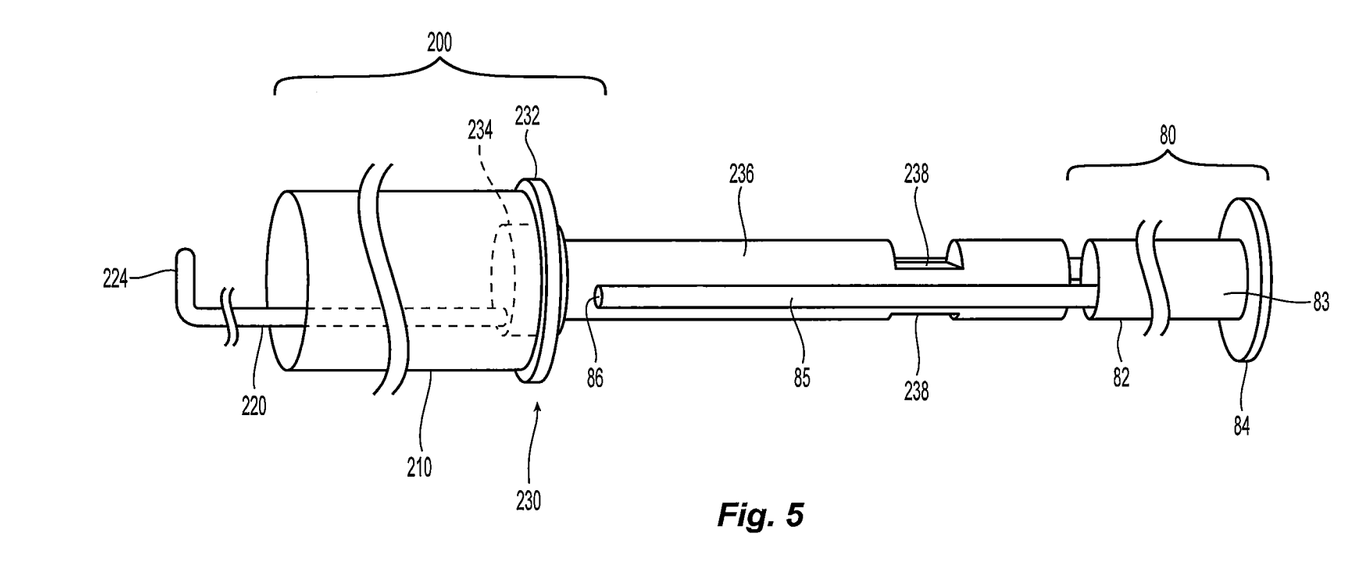
FIG. 5 is a perspective view of the selector assembly and the monopolar assembly of the forceps of FIG. 1.

As shown in FIGS. 4 and 5, proximal hub assembly 230 includes an outer collar 232, an inner base 234, and an elongated member 236. Outer collar 232 is coupled to insulative sleeve 210 at the proximal end of insulative sleeve 210. Inner base 234 is coupled to energizable rod member 220 at the proximal end of energizable rod member 220. As such, translation of proximal hub assembly 230 through housing 20 translates insulative sleeve 210 and energizable rod member 220 together between their respective storage and deployed positions. More specifically, both insulative sleeve 210 and energizable rod member 220 are coupled to proximal hub assembly 230 such that insulative sleeve 210 and energizable rod member 220 are capable of being moved together between their respective storage positions (FIG. 2B), e.g., the storage condition of deployable monopolar assembly 200, and their respective deployed positions (FIG. 2D), e.g., the deployed condition of deployable monopolar assembly 200, upon selective translation of proximal hub assembly 230 through housing 20, as will be detailed below. Elongated member 236 of proximal hub assembly 230 is coupled to and extends proximally from inner base member 234. Elongated member 236 defines a generally cylindrical-shaped configuration, although other configurations are also contemplated, and includes a pair of opposed engagement cut-outs 238 defined therein towards the proximal end thereof, the importance of which is detailed below.

The biasing member (not shown) of deployable monopolar assembly 200 may be positioned about insulative sleeve 210 distally of outer collar 232 of proximal hub assembly 230, within insulative sleeve distally of inner base 234 of proximal hub assembly 230, or in any other suitable position so as to bias proximal hub assembly 230 and, thus, insulative sleeve 210 and energizable rod member 220 proximally towards the respective storage positions thereof, although other suitable biasing members and/or biasing configurations are also contemplated.

With reference to FIGS. 1 and 4, handle assembly 30 includes a movable handle 40 and a fixed handle 50. Fixed handle 50 is integrally associated with housing 20 and movable handle 40 is movable relative to fixed handle 50. Movable handle 40 is movable relative to fixed handle 50 between an initial position, wherein movable handle 40 is spaced from fixed handle 50, and a compressed position, wherein movable handle 40 is compressed towards fixed handle 50. A biasing member (not shown) may be provided to bias movable handle 40 towards the initial position.

Movable handle 40 is ultimately connected to a drive assembly 140 (portions removed from FIG. 4) that, together, mechanically cooperate to impart movement of jaw members 110, 120 between the spaced-apart position (FIG. 2A), corresponding to the initial position of movable handle 40, and the approximated position (FIG. 2B), corresponding to the compressed position of movable handle 40. Any suitable drive assembly 140 for this purpose may be provided.

Figure 3A:
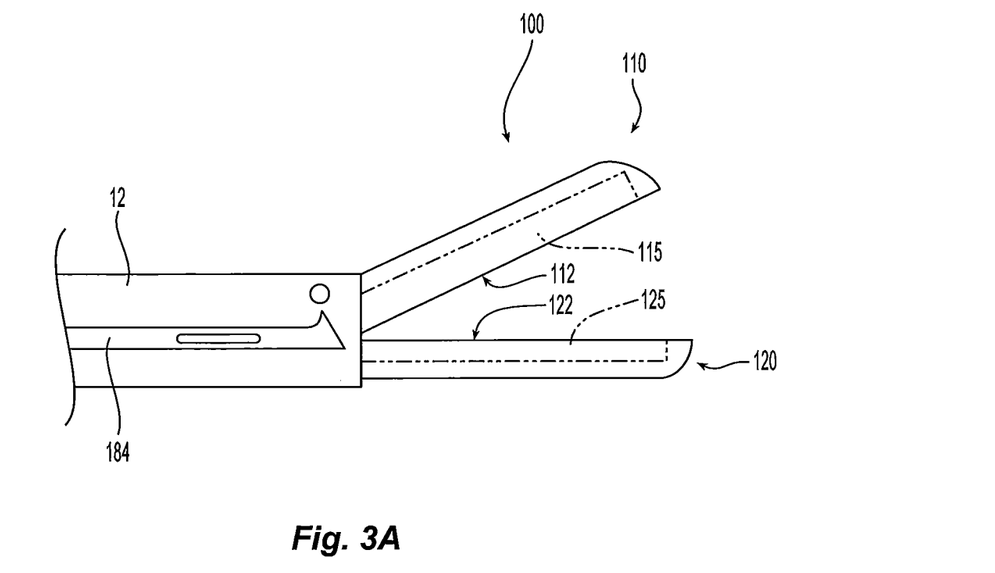
FIG. 3A is a longitudinal, cross-sectional view of the end effector assembly of FIG. 2A with the jaw members disposed in the spaced-apart position and wherein the knife is disposed in a retracted position.
Figure 3B:
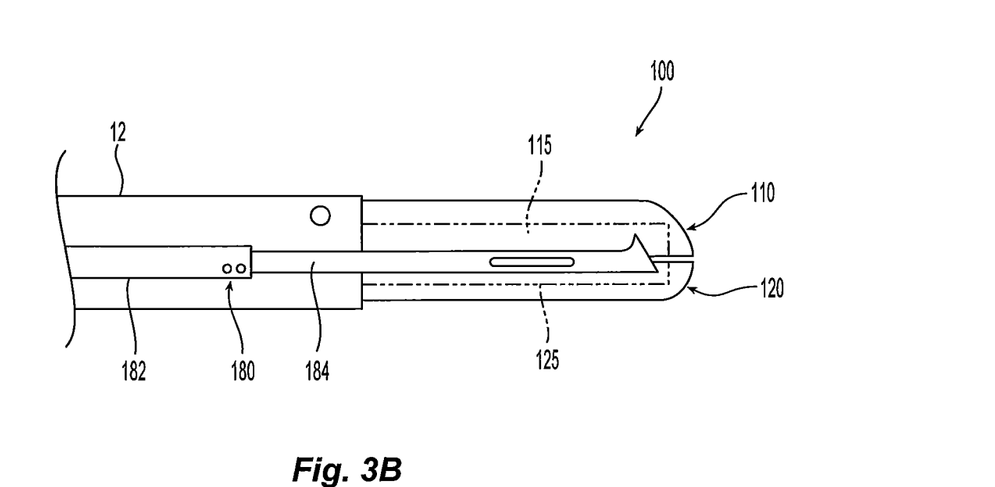
FIG. 3B is a longitudinal, cross-sectional view of the end effector assembly of FIG. 2A with the jaw members disposed in the approximated position and wherein the knife is disposed in an extended position.

With additional reference to FIGS. 3A and 3B, trigger assembly 60 includes trigger 62 that is operably coupled to a knife assembly 180 (portions removed from FIG. 4). Knife assembly 180 includes a knife drive bar 182 having a knife 184 extending from the distal end thereof. A knife biasing member (not shown) may be disposed about knife drive bar 182 to bias knife assembly 180 proximally. Trigger 62 of trigger assembly 60 is selectively actuatable from an unactuated position to an actuated position to advance knife 184 from a retracted position (FIG. 3A), wherein knife 184 is disposed proximally of jaw members 110, 120, to an extended position (FIG. 3B), wherein knife 184 extends at least partially between jaw members 110, 120 and through knife channels 115, 125, respectively, to cut tissue grasped between jaw members 110, 120.

Referring to FIGS. 1 and 4-6C, selector assembly 80 is translatable relative to housing 20 between an inserted position (FIGS. 1 and 6A), wherein selector assembly 80 is substantially disposed within housing 20, and a withdrawn position (FIGS. 6B and 6C), wherein selector assembly 80 extends further proximally from housing 20. When disposed in the withdrawn position, selector assembly 80 is transitionable between first orientation corresponding to a first state of selector assembly 80 (see FIG. 6B), wherein selector assembly 80 is disengaged from deployable monopolar assembly 200, e.g., such that deployable monopolar assembly 200 remains disposed in the storage condition regardless of the translation of selector assembly 80, and a second orientation corresponding to a second state of selector assembly 80 (see FIG. 6C), wherein selector assembly 80 is engaged with deployable monopolar assembly 200 such that selector assembly 80 may be translated between the withdrawn position and the inserted position for selectively transitioning deployable monopolar assembly 200 between the storage condition and the deployed condition, respectively.

Selector assembly 80, as noted above, is rotatable and translatable relative to housing 20, and includes a plunger 82 and a pair of spaced-apart arms 85 extending distally from plunger 82. Plunger 82 extends proximally through an aperture defined within housing 20 and includes a body portion 83 and a manipulation knob 84 that facilitates manual manipulation of plunger 82 from the exterior of housing 20. Arms 85 extend distally from plunger 82 through housing 20 and are positioned on opposed sides of elongated member 236 of deployable monopolar assembly 200. Each arm 85 includes a free end having an inwardly-extending tab 86 disposed thereon. In the inserted position of selector assembly 80 (FIGS. 1 and 6A), tabs 86 of arms 85 are positioned adjacent the distal end of elongated member 236. In the withdrawn position of selector assembly 80 (FIGS. 6B and 6C), tabs 86 of arms 85 are positioned adjacent cut-outs 238 defined within elongated member 236. More specifically, with selector assembly 80 disposed in the withdrawn position and the first orientation (FIG. 6B), tabs 86 of arms 85 are rotationally offset from respective cut-outs 238 of elongated member 236 such that selector assembly 80 remains disengaged from deployable monopolar assembly 200. When selector assembly 80 is rotated to the second orientation (FIG. 6C), tabs 86 of arms 85 are positioned adjacent respective cut-outs 238 of elongated member 236. The free ends of arms 85 may be resiliently biased towards a generally linear configuration, may be resiliently biased inwardly towards one another, or may be otherwise configured such that, with selector assembly 80 disposed in the withdrawn position and the second orientation, tabs 86 of arms 85 are engaged within cut-outs 238 of elongated member 238 to thereby operably engage selector assembly 80 with deployable monopolar assembly 200. In this engaged condition, translation of selector assembly 80, e.g., via manual translation of plunger 82 relative to housing 20, may be effected to transition deployable monopolar assembly 200 between the storage condition (FIG. 2A) and the deployed condition (FIG. 2D).

Referring generally to FIGS. 1-6C, the use and operation of forceps 10 in both the bipolar mode, e.g., for grasping, treating and/or cutting tissue, and the monopolar mode, e.g., for electrical/electromechanical tissue treatment, is described.

Figure 6A:
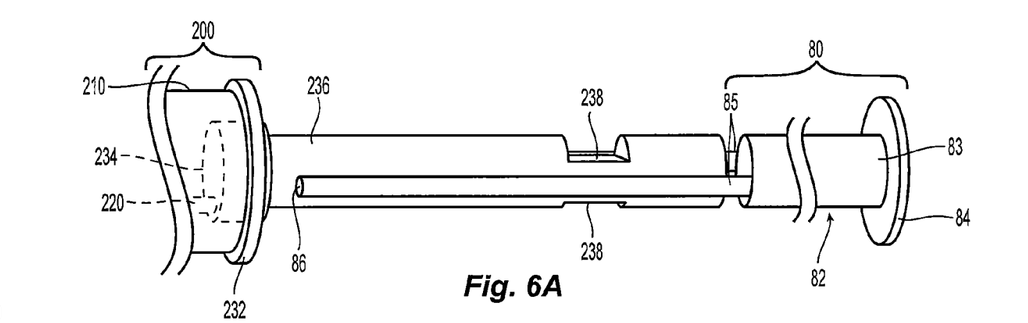
FIG. 6A is a perspective view of the selector assembly of FIG. 5 coupled to the monopolar assembly and disposed in an inserted, disengaged position.
Figure 6B:
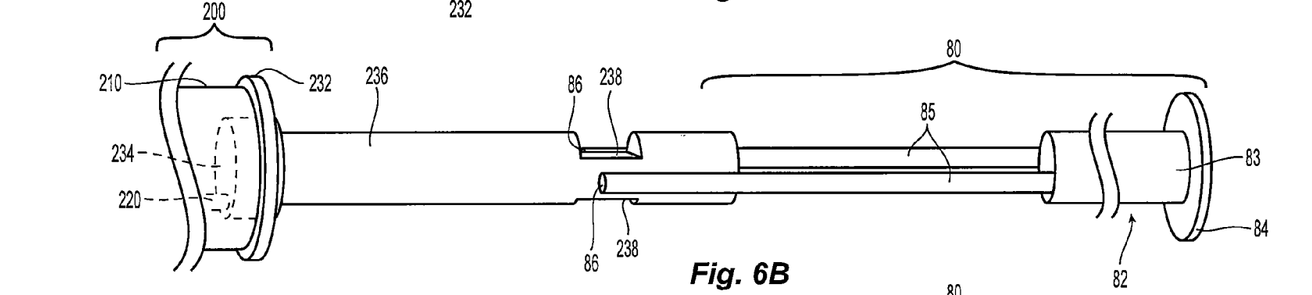
FIG. 6B is a perspective view of the selector assembly of FIG. 5 coupled to the monopolar assembly and disposed in a withdrawn, disengaged position.
Figure 6C:
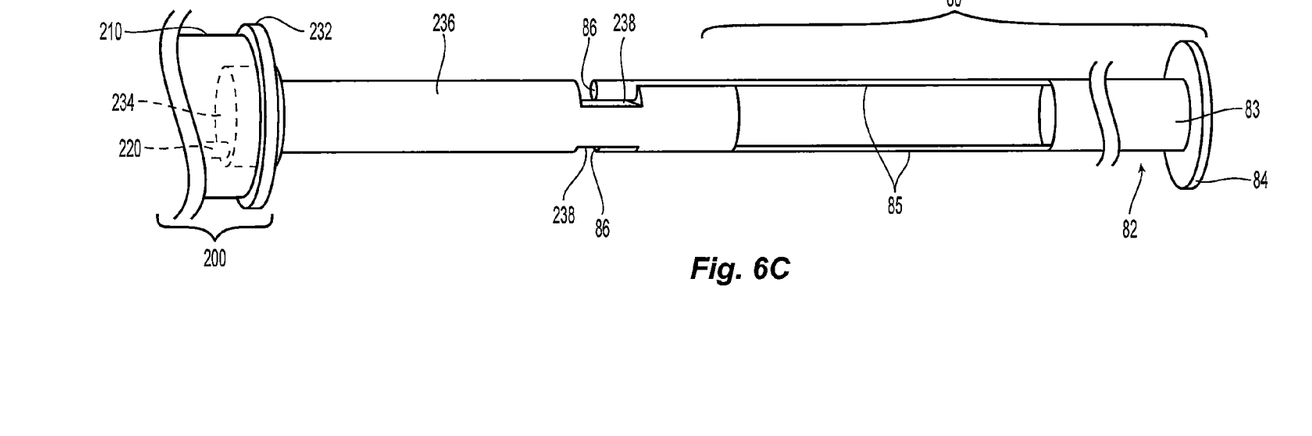
FIG. 6C is a perspective view of the selector assembly of FIG. 5 coupled to the monopolar assembly and disposed in a withdrawn, engaged position.

With respect to use in the bipolar mode, deployable monopolar assembly 200 is disposed in the storage condition (FIG. 2A) and selector assembly 80 is disposed in the inserted position and the first orientation (FIG. 6A). Jaw members 110, 120 are initially disposed in the spaced-apart position and trigger assembly 60 is disposed in the unactuated position such that knife 184 is disposed in the retracted position (FIG. 3A).

With jaw members 110, 120 disposed in the spaced-apart position (FIG. 2A), end effector assembly 100 may be maneuvered into position such that tissue to be grasped, treated, e.g., sealed, and/or cut, is disposed between jaw members 110, 120. Next, movable handle 40 is depressed, or pulled proximally relative to fixed handle 50 such that jaw member 110 is pivoted relative to jaw member 120 from the spaced-apart position to the approximated position to grasp tissue therebetween (FIG. 2B). In this approximated position of jaw members 110, 120, energy may be supplied, e.g., via activation of switch 4, to surface 112 of jaw member 110 and/or surface 122 of jaw member 120 and conducted through tissue to treat tissue, e.g., to effect a tissue seal or otherwise treat tissue in the bipolar mode of operation.

Once tissue treatment is complete (or to cut untreated tissue), knife 184 of knife assembly 180 may be deployed from within shaft 12 to between jaw members 110, 120, e.g., via actuation of trigger 62 of trigger assembly 60 (see FIG. 1), to cut tissue grasped therebetween (see FIGS. 3A and 3B). When tissue cutting is complete, trigger 62 may be released to allow knife 184 to return under bias to the retracted position. Thereafter, jaw members 110, 120 may be moved back to the spaced-apart position (FIG. 2A) to release the treated and/or divided tissue.

As noted above, in the bipolar mode, deployable monopolar assembly 200 is disposed in the storage condition (FIG. 2A) and selector assembly 80 is disposed in the inserted position and the first orientation (FIG. 6A). In order to prepare forceps 10 for use in the monopolar mode, selector assembly 80 is initially translated proximally from the inserted position (FIG. 6A) to the withdrawn position (FIG. 6B), e.g., via grasping and manually translating manipulation knob 84 of plunger 82 proximally relative to housing 20. Once the withdrawn position of selector assembly 80 has been achieved, selector assembly 80 is rotated from the first orientation (FIG. 6B) to the second orientation (FIG. 6C) to engage selector assembly 80 with deployable monopolar assembly 200 as detailed above. Upon such engagement, selector assembly 80 may thereafter be translated distally, e.g., further into housing 20, to transition deployable monopolar assembly 200 from the storage condition (FIG. 2A) to the deployed condition (FIG. 2D).

With deployable monopolar assembly 200 disposed in the deployed condition, activation switch 4 may be actuated to supply energy to energizable rod member 220 of deployable monopolar assembly 200 to treat tissue with monopolar energy. Once tissue treatment and/or other use of deployable monopolar assembly 200 is complete, manipulation knob 84 of selector assembly 80 may be translated proximally, e.g., withdrawn from housing 20, such that deployable monopolar assembly 200 is transitioned from the deployed condition (FIG. 2D) back to the storage condition (FIG. 2A). Thereafter, selector assembly 80 may be rotated back to the first orientation (FIG. 6B) to disengage deployable monopolar assembly 200 from selector assembly 80 and, ultimately, back to the inserted position (FIG. 6A) to retain deployable monopolar assembly 200 in the storage condition (FIG. 2A).

From the foregoing and with reference to the various drawing figures, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a housing;
    a shaft extending distally from the housing;
    an end effector assembly disposed at a distal end of the shaft;
    a deployable assembly selectively movable relative to the end effector assembly between a storage position and a deployed position; and
    a selector assembly operably associated with the deployable assembly, the selector assembly including a selector member extending from the housing for manual manipulation thereof, the selector member manually translatable relative to the housing between a first position and a second position, wherein, in the second position of the selector member, the selector member is manually rotatable relative to the housing for transitioning the selector assembly between a first state, wherein the selector member is decoupled relative to the deployable assembly, and a second state, wherein the selector member is coupled to the deployable assembly such that movement of the selector member from the second position to the first position effects movement of the deployable assembly from the storage position to the deployed position,
    wherein the deployable assembly includes an energizable member and an insulative sleeve, the energizable member and insulative sleeve configured to move together between the storage position and the deployed position, and wherein, in the deployed position, the insulative sleeve is disposed about the end effector assembly and the energizable member extends distally from the end effector assembly.

2. The surgical instrument according to claim 1, wherein the end effector assembly includes first and second jaw members, at least one of the jaw members movable relative to the other between a spaced-apart position and an approximated position for grasping tissue therebetween.

3. The surgical instrument according to claim 2, wherein each of the first and second jaw members includes an electrically-conductive tissue-contacting surface, the electrically-conductive tissue-contacting surfaces configured to conduct energy therebetween and through tissue grasped between the first and second jaw members to treat tissue in a bipolar mode.

4. The surgical instrument according to claim 1, wherein the energizable member is configured to conduct energy to tissue to treat tissue in a monopolar mode.

5. The surgical instrument according to claim 1, wherein the first position of the selector member corresponds to a more-distal position of the selector member relative to the housing, and wherein the second position of the selector member corresponds to a more-proximal position of the selector member relative to the housing.

6. The surgical instrument according to claim 1, wherein the deployable assembly includes an elongate member defining at least one cut-out, and wherein the selector assembly includes at least one arm defining at least one tab, each tab configured for receipt within one of the cut-outs when the selector member is disposed in the second position and the second state to engage the selector assembly with the deployable assembly.

7. The surgical instrument according to claim 1, wherein, in the first state of the selector member, the deployable assembly is maintained in position during movement of the selector member between the first and second positions.

8. A surgical instrument, comprising:
    a housing;
    a shaft extending distally from the housing;
    an end effector assembly disposed at a distal end of the shaft, the end effector assembly including first and second jaw members, at least one of the first and second jaw members movable relative to the other between a spaced-apart position and an approximated position for grasping tissue therebetween, the first and second jaw members configured to conduct energy therebetween and through tissue grasped therebetween to treat tissue in a bipolar mode;
    a deployable assembly including an insulative sleeve and an energizable member, the deployable assembly selectively movable relative to the end effector assembly between a storage position, wherein the insulative sleeve and the energizable member are positioned proximally of the end effector assembly, and a deployed position, wherein the insulative sleeve is disposed about the end effector assembly and the energizable member extends distally from the end effector assembly; and
    a selector assembly operably associated with the deployable assembly and transitionable between a disengaged condition, wherein the selector assembly is disengaged from the deployable assembly such that the deployable assembly is unaffected by movement of the selector assembly, and an engaged condition, wherein the selector assembly is engaged with the deployable assembly such that movement of the selector assembly moves the deployable assembly between the storage position and the deployed position.

9. The surgical instrument according to claim 8, wherein the selector assembly includes a selector member translatable relative to the housing between an inserted position, wherein the selector member extends into the housing, and a withdrawn position, wherein the selector member extends proximally from the housing, for moving the deployable assembly between the storage position and the deployed position when the selector assembly is disposed in the engaged condition.

10. The surgical instrument according to claim 9, wherein the deployable assembly is maintained in its position upon translation of the selector member between the inserted and withdrawn positions with the selector assembly disposed in the disengaged condition.

11. The surgical instrument according to claim 9, wherein rotation of the selector member from a first orientation to a second orientation with the selector member disposed in the withdrawn position transitions the selector assembly from the disengaged condition to the engaged condition.

12. The surgical instrument according to claim 9, wherein the deployable assembly includes an elongate member defining at least one cut-out, and wherein the selector assembly includes at least one arm defining at least one tab, each tab received within one of the cut-outs when the selector assembly is disposed in the engaged condition to engage the selector assembly with the deployable assembly.

13. The surgical instrument according to claim 12, wherein the at least one tab is offset from the respective cut-out in the disengaged condition of the selector assembly.

* * * * *